Figure 1:
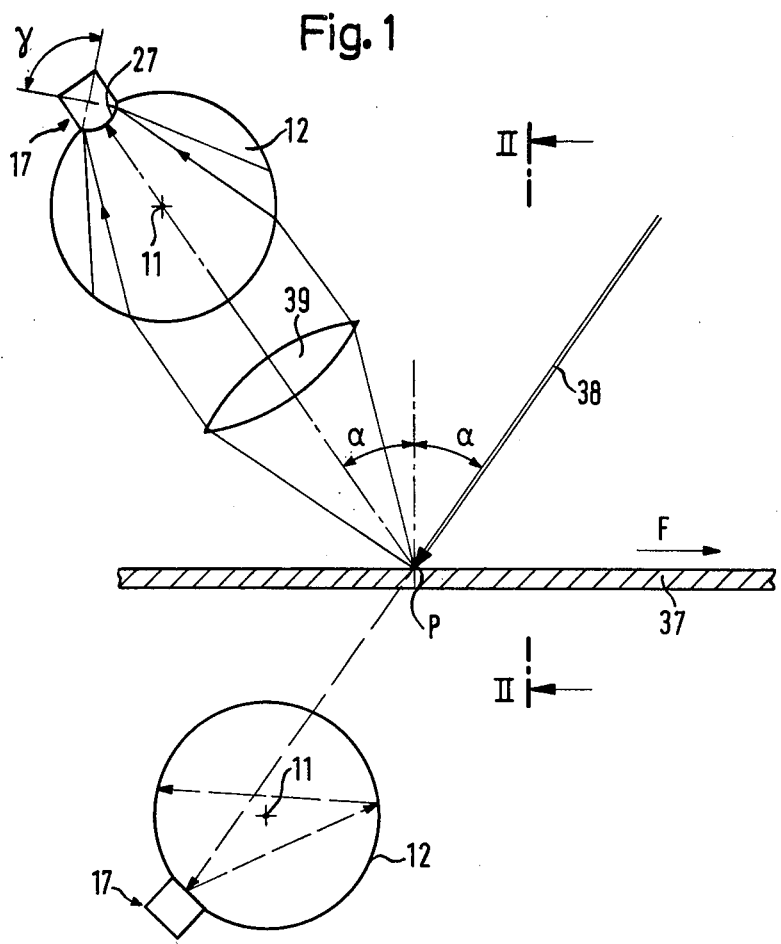

United States Patent [19]
Sick et al.

[11] 4,200,397
[45] Apr. 29, 1980

[54] APPARATUS FOR DISTINGUISHING BETWEEN PREDETERMINED RANGES OF ANGLES AT WHICH LIGHT RAYS LEAVE A SURFACE

[75] Inventors: Erwin Sick, Icking; Klaus Hartmann, München; Heinz Henneberger, Stockdorf, all of Fed. Rep. of Germany

[73] Assignee: Erwin Sick GmbH Optik-Elektronik, Waldkirch, Fed. Rep. of Germany

[21] Appl. No.: 914,802

[22] Filed: Jun. 12, 1978

[30] Foreign Application Priority Data

Jun. 21, 1977 [DE] Fed. Rep. of Germany ....... 2727927

[51] Int. Cl.² .......................................... G02B 27/00
[52] U.S. Cl. .................................. 356/429; 250/227; 356/238
[58] Field of Search ................... 250/571, 572, 227; 356/238, 431, 430, 429

[56] References Cited

U.S. PATENT DOCUMENTS

| | | | |
|---|---|---|---|
| 3,777,149 | 12/1973 | Marcatili | 250/227 |
| 4,004,152 | 1/1977 | Obser et al. | 356/431 |
| 4,038,554 | 7/1977 | Craig | 356/431 |
| 4,085,322 | 4/1978 | Sick | 250/227 |
| 4,116,527 | 9/1978 | Sick | 356/431 |

Primary Examiner—John K. Corbin
Assistant Examiner—R. A. Rosenberger

[57] ABSTRACT

The flanks of faults present in a surface produce abnormal reflection of a laser beam during linewise scanning of the surface by a laser beam. This apparatus deflects the angles of reflection from the surface, to indicate the presence of a flank, by a light conducting rod arranged parallel to the direction of linewise scanning for receiving reflected light on its surface and for conducting this light to its end face. The various light rays spread out transversely to the direction of scanning during their passage through the light conducting rod and are detected as they pass through a series of concentric annular apertures spaced from the end face of the light conducting rod. Each aperture is associated with a particular range of angles of incidence irrespective of the point on incidence along the surface of the rod and photoelectric detectors are used to sense the light passing through each aperture to provide the necessary indication of the presence or non-presence of a fault. Several types of transparent light guides are used to concentrate the light from the apertures onto the photoelectric detector and various signal processing circuits are described.

60 Claims, 16 Drawing Figures

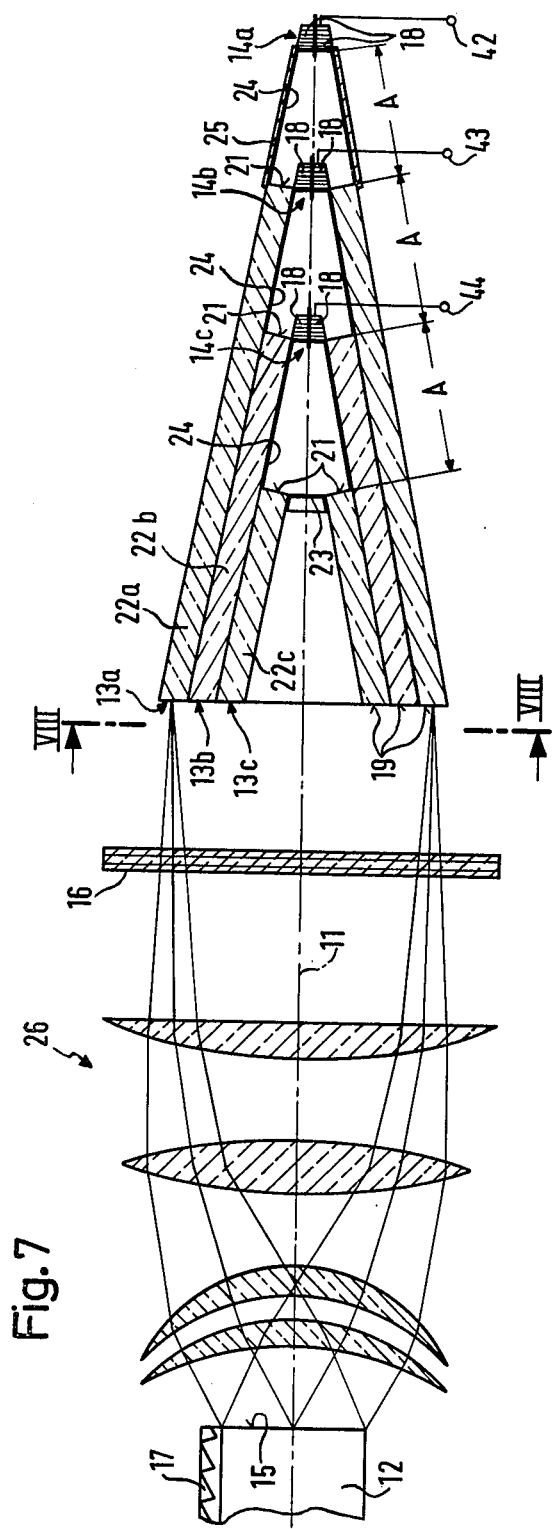
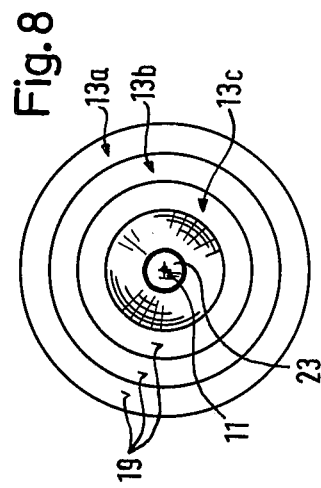

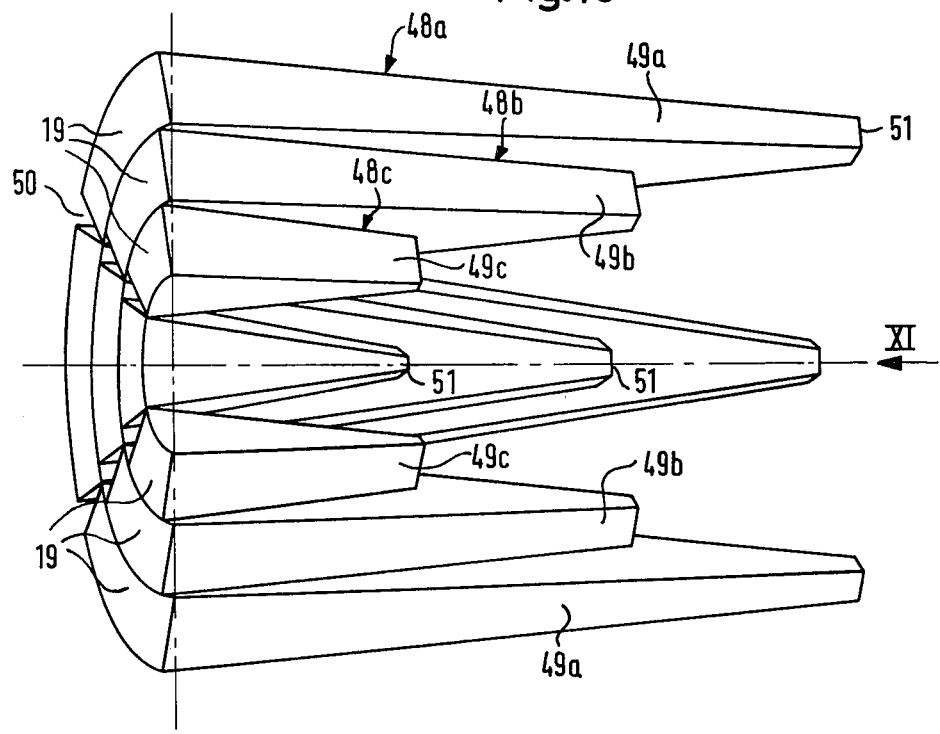
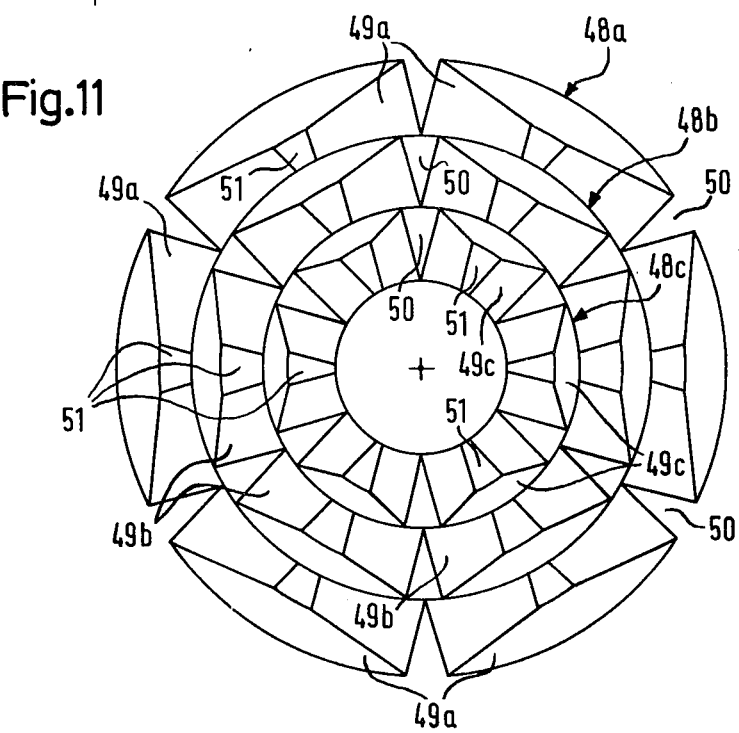

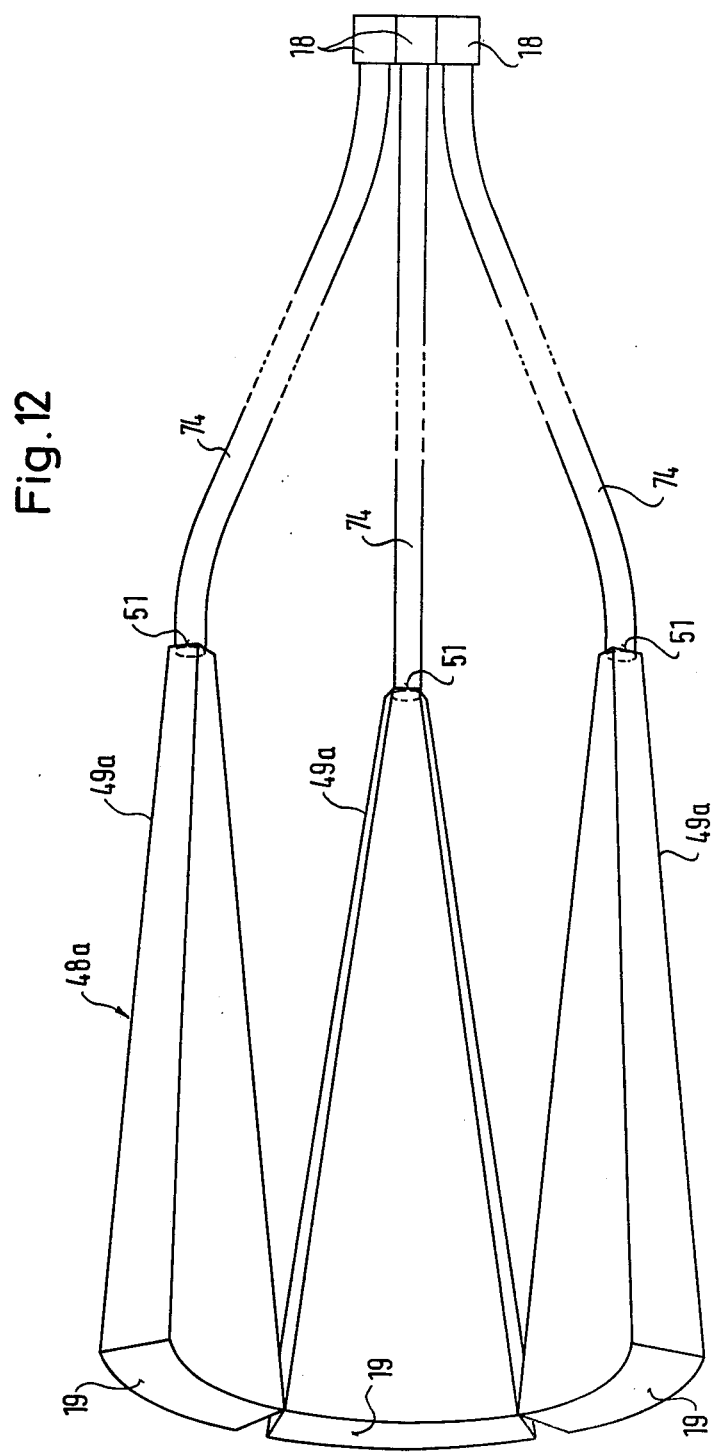

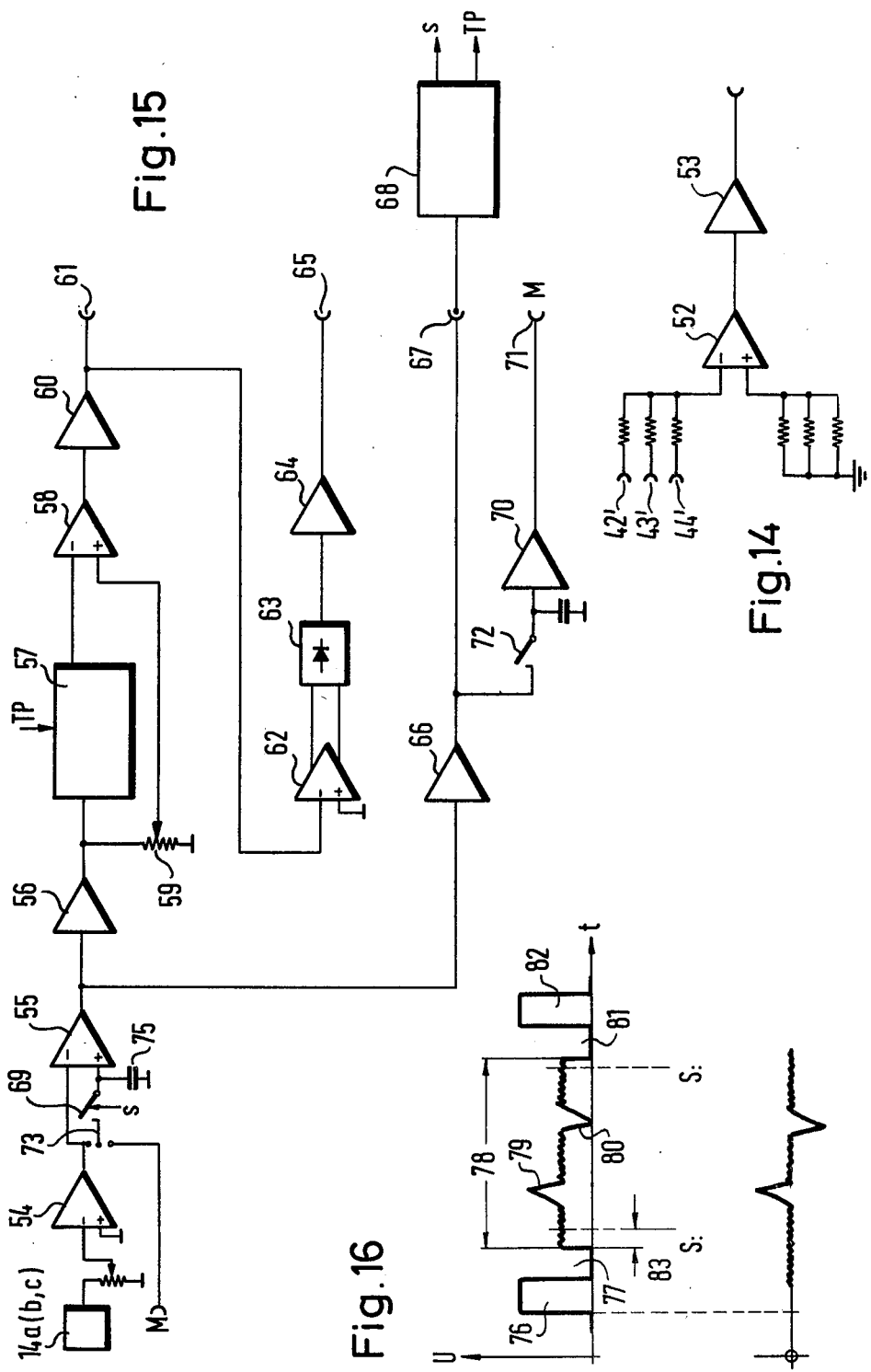

APPARATUS FOR DISTINGUISHING BETWEEN PREDETERMINED RANGES OF ANGLES AT WHICH LIGHT RAYS LEAVE A SURFACE

The invention relates to an apparatus for distinguishing between predetermined ranges of angles at which light rays leave a point of a surface in a plane, and has particular reference to apparatus of the kind in which a light conducting rod is arranged parallel to the plane, receives the light rays on its surface, and carries a stepped mirror arrangement disposed parallel to the rod axis on the surface of the rod opposite to the light entry side and which reflects the incident light to the interior of the rod under angles of total reflection so that it reaches one end face of the light conducting rod where it impinges at various angles to the rod axis on photoelectric convertors whose electrical output signals are a measure of the angle at which the incident light leaves the point and in which the spacing of the photoelectric convertor from the light exit end face of the light conducting rod is of a size such that the light beams from the angular ranges to be distinguished are spatially separated from each other.

In a known apparatus of this kind (DT-OS 25 32 603) a light conducting rod of rectangular section is especially used in order to achieve a clear association between entry angle and the operative photoelectric convertor. Because of the spatial extent of the individual photo convertors no strong association exists between convertors and individual angles rather solely particular angular ranges whose size depends on the extent of the photoelectric convertors and their spacing from the end face of the light conducting rod.

In the known apparatus the photoelectric convertors are arranged in the form of a surface matrix in order to make it possible to distinguish between as many angles lying in different planes as possible.

The provision of a clear association between angular ranges and the surfacelike arrangement of convertors however requires stringent controls on the quality of the light conducting rod which is of either rectangular or quadrilateral section. Even trivial inaccuracies in the surfaces which bring about total reflection, such as striations and possibly air inclusions, can disadvantageously affect the intended clear association.

The further away from the light exit surface of the light conducting rod the light enters the surface of the light conducting the rod the more critical becomes the association between the angle at which the light leaves the surface under consideration and a photoelectric convertor of the convertormatrix.

The object of the present invention is to provide a simply constructed and economically manufactured apparatus of the kind named above which, by limiting it to distinguishing between only a few angular ranges, which all lie in a plane which preferably includes the axis of the rod, allows a clear association between the angular ranges and the photoelectric convertors even when the light conducting rod does not satisfy the most stringent optical requirements.

According to the present invention there is provided apparatus suitable for distinguishing between predetermined ranges of angles at which light rays leave a point on a surface, the apparatus comprising a light conducting rod of substantially circular section said light conducting rod being disposed parallel to the surface for receiving light rays reflected from the point onto its surface and having means capable of transmitting said light rays to an end face of the light conducting rod and producing at the end face of the rod an angular separation of the emergent light rays said angular separation being related to the angle of incidence of said light ray along the rod relative to the optical axis thereof, there being further provided several photoelectric detector arrangements spaced apart from the end face of said light conducting rod and each disposed to receive the light from at least a major portion of a respective one of a series of annular apertures through which said angularly separated light leaving said light conducting rod passes, each said aperture and its associated detector being associated with a particular range of angles. Several forms of light conducting rod can be used in the apparatus provided that they are able to produce the necessary angular separation of the emergent light rays. In one form the light conducting rod has a stepped mirror arrangement along its side opposite to the light entry side and is so arranged that at least the largest part of the light entering into the light conducting rod impinges onto the individual mirrors of the stepped mirror arrangement in a plane at right angles to the axis of the rod and at such angles that the light reflected from the individual mirrors, after a single total reflection on the wall of the light conducting rod, does not once more impinge onto the stepped mirror arrangement. This requirement can be satisfied either by a sharply defined light ray impinging obliquely onto the stepped mirror arrangement, or through a light beam which uses the entire aperture of the light conducting rod and which is focussed onto the stepped mirror arrangement, or also by using individual mirrors convexly curved in the plane at right angles to the axis of the rod.

The basic thought of the invention is thus to be seen in tha by limiting the determination of angular ranges to a plane which contains the axis of the light conducting rod and by using a light conducting rod of circular cross-section a clear association can be achieved between a few neighbouring angular ranges and correspondingly few photoelectric convertor arrangements.

This clear association is given unchanged irrespective of whether the incident light ray enters the light conducting rod near to or away from the light exit surface of the light conducting rod.

A circular light conducting rod is considerably more satisfactory than the previously used kind of rectangular section because it is considerably easier to manufacture and is not so sensitive to irregularities in the rod.

The preferred use of the invention is for monitoring for faults in material webs, especially those with a reflecting surface, which have an indicatrix with a pronounced reflected main beam (or lobes) and weak side beams or lobes. One is concerned here with such things as copper coated conductive circuit boards, laminates or sheet metal which are to be monitored for faults. Such webs are preferably scanned by a sharply defined laser light beam transversely of their direction of feed.

The reflected light is received by a light conducting rod arranged parallel to the scanning direction. the apparatus in accordance with the invention enables an angle of reflection, which deviates from the normal reflection of the flat web surface, to be determined and for conclusions to be drawn therefrom as to the nature of the associated fault. Further the apparatus of the invention enables certain faults to be determined which would not otherwise be found.

The apparatus in accordance with the invention is especially appealing for determining the presence of bumps or depressions of the material surface in which continually curved flanks are present. The incident sharply defined beam is reflected at these flanks in another direction than at the undistorted flat surface which results in a pronounced indication of their presence through use of the apparatus of the invention.

For the solution of the problem of the invention there are preferably provided from two to four and especially three concentric apertures. The arrangement in this case is usefully such that the middle one of the three concentric apertures received the light normally reflected at the plane surface whilst both neighbouring concentric rings normally receive little or no scattered light. If however the incident light is reflected from the flank of a bump or depression then one of the two neighbouring apertures will also receive light which leads to a pronounced indication signal at the output of the associated photoelectric convertor arrangement because the two neighbouring rings concentric with the middle aperture are working in the dark region. In the simplest case two concentric apertures would also suffice for the recognition of faults but should however be so spaced apart from each other in the radial direction that they do not receive any normally reflected light but rather operate in the dark region.

Light scattering means can be arranged between the rings and the end face of the light conducting rod such that the individual light rays are fanned out without removing the clear association between angular ranges and apertures.

This is useful for delivering as uniform an electrical output signal as possible when the light rays associated with the individual apertures are too sharp.

A desired amount of smoothing of the electrical output signal can be achieved by the light scattering means. The light scattering means is preferably formed by a lenticular screen whose scattering effect is not too large so that the clear angular association is maintained.

In the simplest case the invention can be realised in that interconnected individual convertors are arranged a the apertures, or the aperture, so as to sense the aperture as completely as possible and to form a photoelectric detector arrangement giving a single electrical output signal.

It is especially useful in this embodiment to provide the light scattering means in order to avoid too localised impingement of the light rays leaving the light conducting rod on the individual convertors.

A significant smoothing of the signal can be achieved when the end faces of concentric transparent hollow, or respectively, solid cylinders form the apertures and respective photoelectric detector arrangements are arranged at the other end faces of the cylinders. Inside the individual cylinder the light is guided forwards by total reflection at the walls whereby; on account of the optical irregularities of the transparent hollow cylinders, which in this case are thoroughly desirable, a blurring effect is achieved so that on the entry of a pronouncedly individual light ray a considerably smoothed light beam is fanned out at the outlet.

If very small angles relative to the rod axis are to be sensed then the innermost of the concentrically arranged apertures can also be a circle with the rod axis as its centre. Correspondingly the innermost of the concentric hollow cylinders should be constructed as a solid cylinder.

In an especially preferred embodiment the end faces of transparent hollow, or respectively solid, truncated circular cones are arranged at the apertures and their other end faces are each respectively provided with a photoelectric detector arrangement.

Whilst the outer truncated cones are hollow, in order that they can be slid over each other, the innermost truncated cone can also be of solid construction if very small angles relative to the rod axis are to be sensed. It must be taken into account in this embodiment that the light entering the end face of the truncated cone is being advanced through the interior to the other end face by total reflection. In this connection the alternating reflection between the opposite walls of a hollow truncated cone is especially suitable so that the innermost truncated cone should also be of hollow construction.

The length of each cylinder or truncated cone should in each case be sufficiently large that the light entering a the one end face is reflected at least once at one of the interior walls.

The embodiment with transparent hollow truncated cones has the further advantage over the embodiment with transparent hollow cylinders that not only is the incident light blurred and therefore made more uniform or smoother but rather that in addition the light emerges from circular rings of smaller diameter. In this way photoelectric detector arrangements with considerably smaller surfaces can be used.

The photoelectric detector arrangements can once more comprise individual convertors which are respectively connected together to sense the associated end face as fully as possible the quantity of the individual convertors can however be considerably reduced.

It is of especial advantage when the lengths of the truncated cones from the outer to the inner become stepwise smaller so that the detector arrangements associated with the individual truncated cones are arranged axially behind one another. By this construction the space required for the detector arrangements in the radial direction is also reduced.

In as much as each detector arrangement is axially spaced from the associated end face a concentration of the light onto a small surface region can be brought about of such a kind that each detector arrangement only needs to comprise an individual convertor. In this way a very significant simplification and improvement in the operational capability is achieved.

In order to deflect as much light as possible onto photoelectric detector arrangements arranged in this way, and in accordance with a further advantageous embodiment, the interior wall of each truncated cone from the end face of the next inner truncated cone to its own end face is provided with a mirror surface.

The outer surface of the outermost truncated cone should in this connection be extended to the associated detector arrangement by a wall which continues the truncated cone shape and which carries an internal mirror surface. A constructionally very compact, and nevertheless however also an optically completely satisfactory arrangement, is provided in which the convertor arrangement associated with the one truncated cone is respectively arranged inside the inner border of the end face of the next outer truncated cone. The wall connected to the exterior surface of the outermost truncated cone should be sufficiently long that its inner border is of the same size as the inner border of the other truncated cones.

This embodiment especially allows all the individual detector to be of the same size and construction. In the preferred embodiment with three concentric hollow truncated cones only three individual detector ae thus necessary which are available at a favourable cost in the form of photodiodes.

By the concentration of the light which is received via an aperture of relatively large diameter onto the relatively small surface region of a photodiode the insertion of a photoelectronic multiplier (photomultiplier), which is in many respects disadvantageous, has been avoided.

It is of especial advantage if the end faces of transparent tapering light guides are arranged at the rings, the photoelectric detector arrangements being in optical contact with the other end faces of the tapering light guides.

In order to limit the size of the concentric apertures, to deflect as much light as possible onto these apertures and to hold the entire arrangement as compact as possible a lens system is preferably arranged between the apertures and the end face of the light conducting rod to concentrate the light leaving the light conducting rod at the specified angles onto the individual apertures.

It is usefully to be taken into account that the lens system should deflect the light so as to subtend as small an angle as possible to the surface of the cylinder, or truncated cone or light guide. In this way an especially loss free conduction of the light is brought about.

The concentric arrangement of the light receiving apertures makes possible a trouble free association of the angular ranges even when, in accordance with an especially advantageous embodiment, the stepped mirror arrangement comprises convexly curved individual mirrors in a plane at right angles to the axis of the rod, the convex curvature of which is preferably such that, after reflection, a parallel light beam incident on the individual mirror is fanned out by from 10° to 90° and preferably by 50° in the plane of curvature. The fanning out thus takes place in a plane which runs at right angles to the plane in which the angular ranges to be determined are found.

For this reason the fanning out does not disadvantageously effect the clear association between angular range and photoelectric detector arrangements. On the other hand the strong spreading out of the incident light by the convexly curved individual mirrors does guarantee an exceptional uniformity of the light which finally falls onto the photoelectric detector arrangement. Apart from this, the disturbing influence of the stepped mirror arranged on the light conduction along the light conducting rod is considerably alleviated by the use of the convexly curved individual mirrors.

The apparatus of the invention is especially suitable for recognising faults in a reflecting material which an indicatrix having a pronounced main reflection lobe (or beam) and weak secondary lobes or because in which a sharply defined laser beam continually scans the surface of the material, the light conducting rod is arranged parallel to the surface of the web of material and to the scanning direction and receives on its surface at least partially the light reflected from the surface.

Embodiments of the invention will now be described by way of example only and with reference to the drawing in which is shown:

FIG. 1 a schematic side view of a light receiving device incorporating a light conducting rod.

Figure 2:
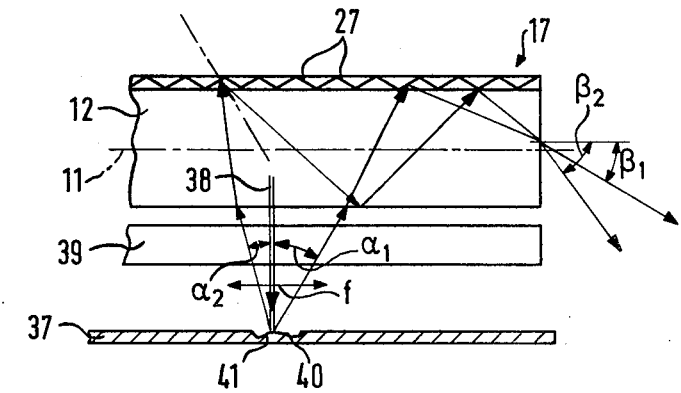

FIG. 2 a section on the line II—II of FIG. 1.

Figure 3:
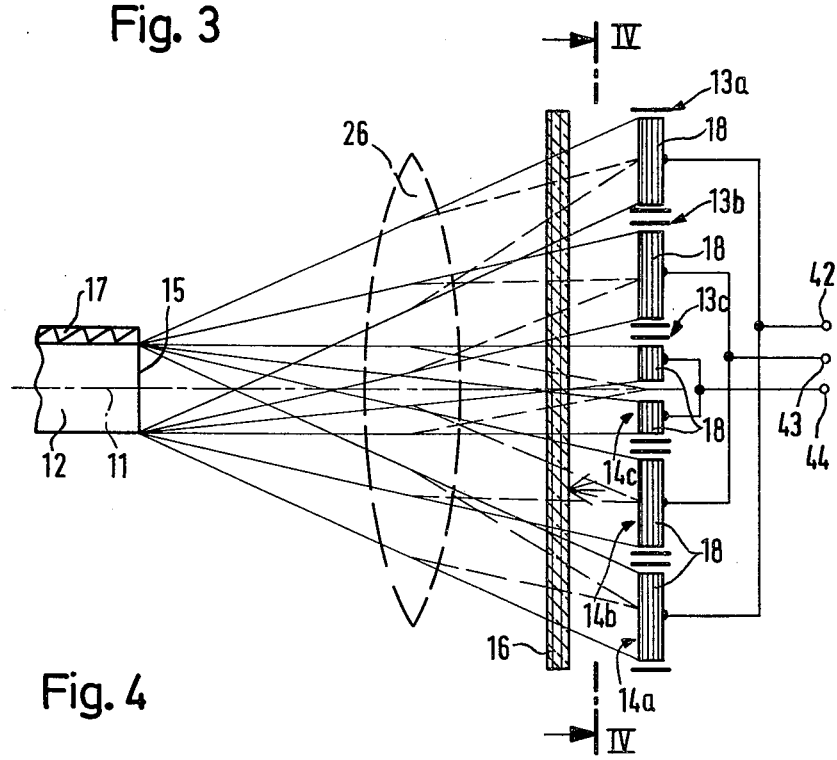

FIG. 3 a schematic partly sectioned side elevation of a very simplified form of the apparatus.

Figure 4:
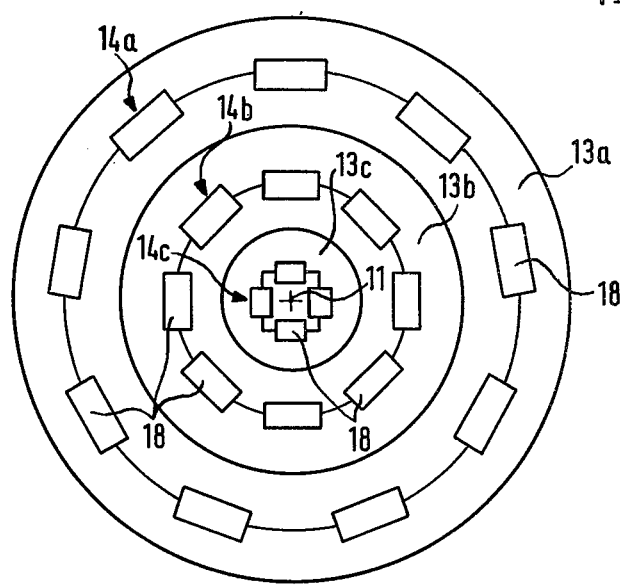

FIG. 4 a view on the line IV—IV of FIG. 3.

Figure 5:
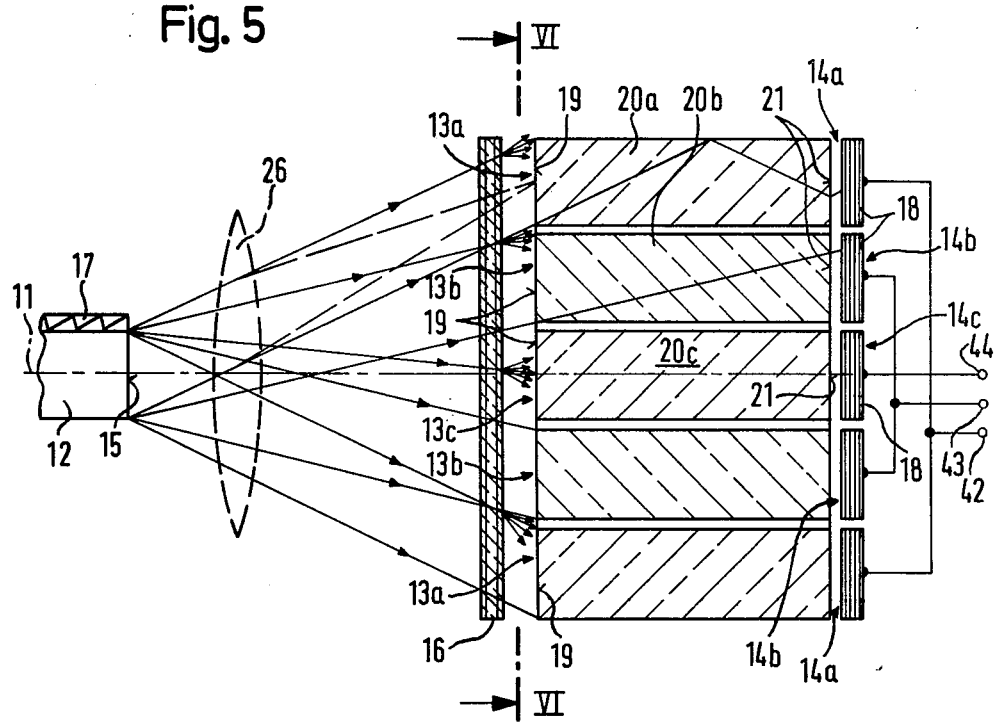

FIG. 5 a partly sectioned schematic side elevation of a further embodiment.

Figure 6:
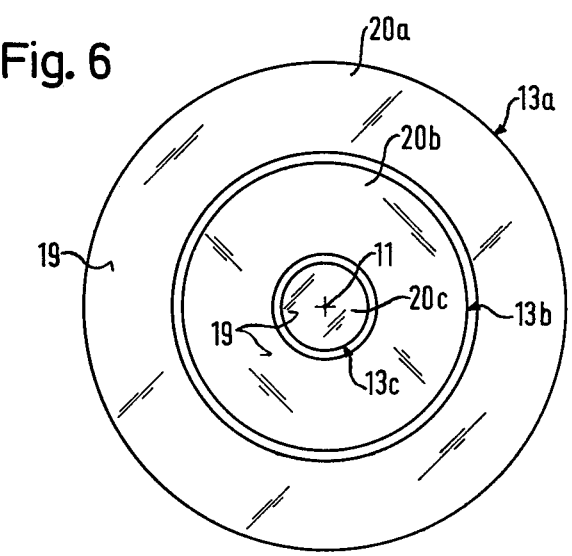

FIG. 6 a view on the line VI—VI of FIG. 5.

FIG. 7 a partly sectioned side view of an especially preferred embodiment.

FIG. 8 a view on the line VIII—VIII of FIG. 7.

Figure 9:
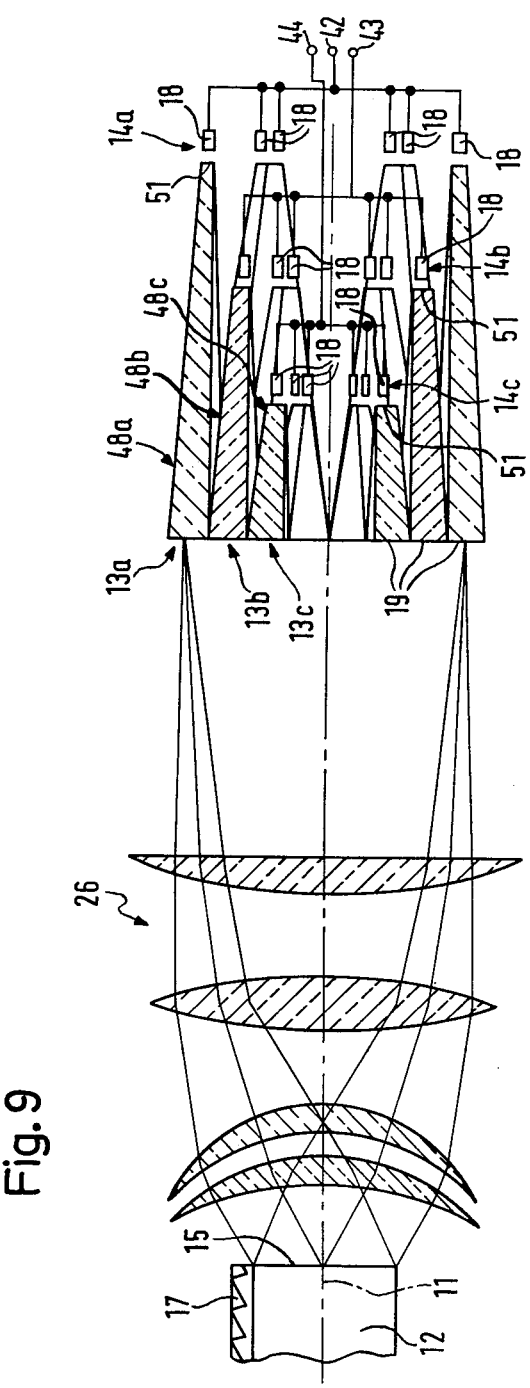

FIG. 9 a partly sectioned side view of a further especially preferred embodiment.

FIG. 10 a perspective illustration of the light focussing part of the embodiment of FIG. 9.

FIG. 11 a view in the direction of the arrow XI in FIG. 10 which however illustrates the whole light focussing device.

FIG. 12 a schematic illustration of the connection of the exit end faces of the light conductors to a common photoelectric convertor by way of light conducting fibres.

Figure 13:
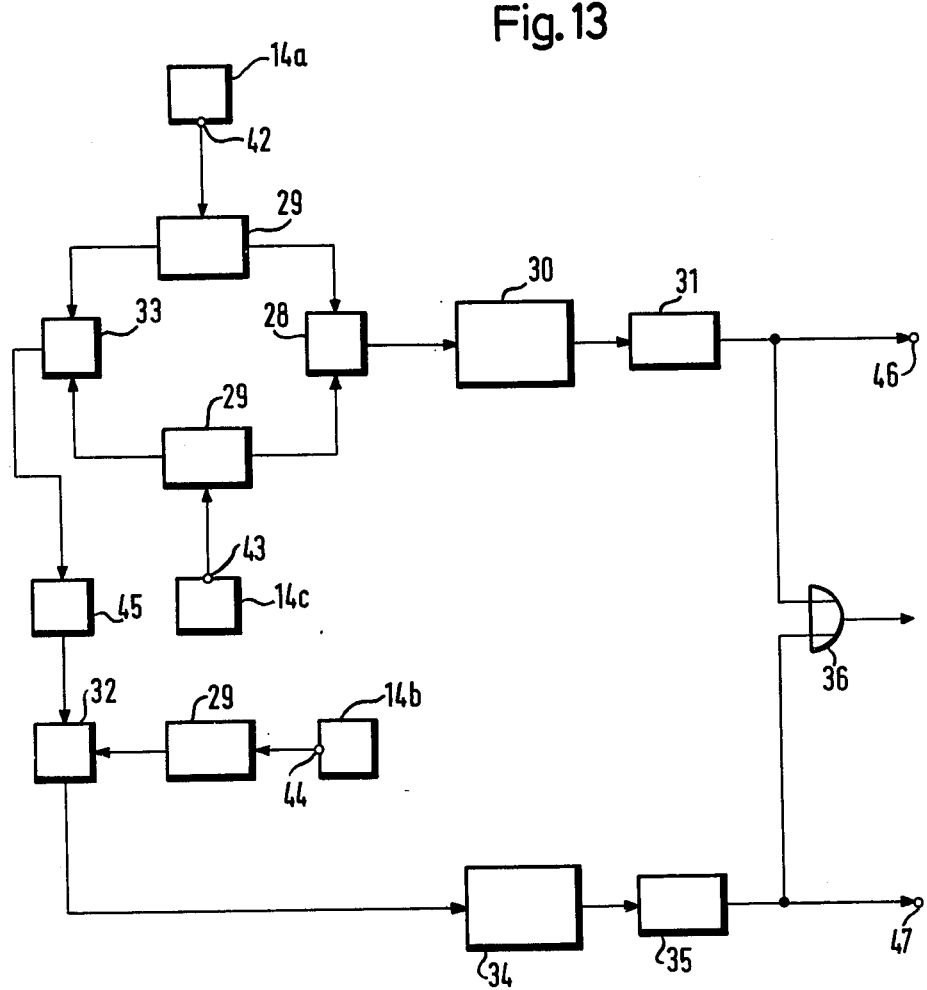

FIG. 13. a preferred circuit arrangement for an apparatus having three photoelectric convertor devices.

FIG. 14. a further preferred circuit diagram for an apparatus having three photoelectric convertor devices.

FIG. 15. a preferred signal processing circuit for the signals of the individual photoelectric convertor devices and FIG. 16. a schematic diagram of the time wise progression of a video signal appearing at the inlet of the circuit arrangement of FIG. 15 on receipt of two faults which give rise to opposite effects.

In FIGS. 1 and 2 a web or plate 37 having a reflecting upper surface, for example a copper coated circuit board, is continually moved in the direction of the arrow F. A laser beam produced in manner not shown impinges, in a plane containing the direction of advance F, at an angle $\alpha$ onto the surface of the web 37. In accordance with FIG. 2 the laser beam 38 executes a periodic scanning movement across the entire width of the web 37. The scanning speed is sufficiently high that, taking account of the speed of advance of the web 37 in the direction of the arrow F, a spaceless linewise scanning of the web is achieved. The scanning direction f and the direction of advance F are at right angles to one another. The light of the laser beam 38 is reflected at the angle of reflection $\alpha$ from the surface of the web 37 to a cylindrical lens 39 which extends parallel to the scanning direction F, and to the web, relatively close to the web. Because however the surface of the web 37 is not a mirror, but rather a reflecting surface with a main reflecting beam and weaker secondary beams, a beam of light leaves the point of impingement P as is illustrated in FIG. 1. The cylindrical lens 39 concentrates the received light beam onto the aperture of a light conducting rod 12 which is arranged parallel to it with its axis 11 parallel to the cylindrical lens. The light conducting rod 12 has a stepped mirror arrangement 12 at its surface opposite to the light entry surface the individual mirrors of which are inclined to the rod axis 11 at an angle such that the incident light is reflected back at angles of total reflection into the interior of the light conducting rod 12. In accordance with FIG. 1 the stepped mirrors are convexly curved so that a parallel incident light beam is spread out after reflection through an angle $\gamma$.

Because the light of FIG. 1 impinges at various angles onto the stepped mirror arrangement 27 and, if necessary is additionally spread out by the convex curvatures of the individual mirrors 27, it is avoided that the reflected light, after one total reflection at the walls of the light conducting rod 12, once more impinges on the stepped mirror arrangement 27. However a certain amount of fanning out is achieved following the reflection without the convexly curved individual mirrors because of the convergent path of the light beam which enters the rod 12 as per FIG. 1.

A further light conducting rod 12 is illustrated beneath the web 37 which receives light in the case of a hole in the web 37. Because, in this case, a sharply defined parallel light ray enters the rod the incident light ray must be sufficiently far removed from the rod axis 11, as is illustrated in FIG. 1, that the light reflected at the stepped mirror arrangement 17 does not fall once more onto the stepped mirror arrangement 17 after a total reflection on the walls of the light conducting rod 12.

The embodiment with transmitted light is of significance when it is expected that apertures provided in the web, or other irregularities will influence the exit angle of the light beam 38. In this connection the apparatus is suitable for use in determining faults in transparent films in which striations are provided which deflect the light beam passing through the film.

Such deflections could also be determined with the apparatus of the invention.

In FIG. 2 two faults 40, 41 are schematically reproduced, of which the one may produce a deflection of the reflected light beam to the right under an angle $\alpha_1$ and the other a deflection of the reflected light to the left through an angle $\alpha_2$.

As can be seen from FIG. 2 the light rays which are differently reflected at the faults 40, 41 leave the light conducting rod at different angles $\beta_1$, $\beta_2$, respectively. This fact is used by the apparatus of the invention for recognising the fault.

The exit angles $\beta_1$, $\beta_2$ remain unchanged relative to the axis of the rod 11, due to the fanning out of the incident light ray in the plane of FIG. 1. They lie however in two different planes which run prallel to the axis 11. The light which enters the light conducting rod under different specified angles (e.g. $\alpha_1$, $\alpha_2$) in the plane of FIG. 2 thus leaves the end face of the rod angularly separated relative to the axis of the rod 11, and is fanned out so as to pass annular ring shaped apertures, at a certain axial distance from the end face. The annular ring shaped apertures comprise the entry apertures of the optical system which is arranged concentric with the axis of the rod 11, downstream of the end face thereof. Each aperture, whose width depends on the diameter of the rod, is associated with an entry angle ($\alpha_1$, $\alpha_2$), and receives a range of angles equally distributed to either side of the means angles ($\alpha_1$, $\alpha_2$).

For receiving the light which succeeds in reaching the individual apertures photoelectric convertor devices 14a, 14b, 14c are provided at a specified distance from the end face 15 of the light conducting rod 12. The photoelectric convertor devices sense light incident concentric non on the overlapping apertures 13a, 13b, 13c. The inner aperture can also be arranged as a full circle 14c as seen in FIGS. 3 and 4.

Each convertor arrangement 14a, 14b respectively 14c, comprises similar photoelectric convertors 18, which are so connected together that each convertor arrangement delivers a single electric output signal which corresponds to the total light flux received by the associated aperture.

In the arrangement illustrated in FIG. 3 three electrical outputs 42, 43 respectively 44 are thus present.

Preferably the parallel beams in the plane of FIG. 3 are concentrated onto the convertor arrangements 14a, 14b respectively 14c by a lens 26 or a lens system separated by its focal length from the apertures 13a, 13b respectively 13c as is illustrated in broken lines in FIG. 3. In this way the separation of the angles is considerably improved because an angle of incidence ($\alpha_1$, $\alpha_2$) corresponds to a line of light in the plane of the apertures 13a, 13b or 13c concentric with the axis of the rod. This holds moreover for all the embodiments.

A light scattering device, for example in the form of a lenticular screen, can also be arranged between the end face 15 and the aperture 13 and indeed especially when the lens 26 is also present.

By the provision of the lens 26 each of the concentric apertures 13a, 13b or the inner circle 13c receives light from a specified angular range in the plane of FIG. 2. The circular aperture 13c of FIGS. 3 and 4 receives most of the light reflected to the right as seen in FIG. 2 (fault 40) whilst the outer aperture 13a receives the light deflected furthest to the left in FIG. 2 (fault 41). The middle aperture 13b receives light so long as no faults are present on the surface of the web.

In this way, with a fault free surface, only the aperture 13b receives light whilst the apertures 13a, 13c are dark. The aperture 13b thus works in the light field and the aperture 13a, or respectively the circular aperture 13c in the dark field.

In the further examples the same reference numerals represent corresponding parts to those in FIGS. 1 to 4.

In FIGS. 5 and 6 concentric transparent hollow cylinders 20a, 20b and a solid cylinder 20c are arranged with their exit and faces in front of the photoelectric detector arrangements 14a, 14b, 14c and and the annular (or circular) end faces 13a, 13b, 13c are then the apertures. The photoelectric detector arrangements 14a, 14b or 14c each comprise several individual convertors 18, are arranged at the exit faces of the cylinders 20 as with the embodiment of FIGS. 3 and 4. A further light scattering arrangement 16 can be provided between the end face 15 of the light conducting rod 12 and the end faces 19 of the cylinders 20.

The insertion of the cylinders 20 between the concentric light receiving rings 13a, 13b, 13c leads to a smoothing of the stream of light so that the detector arrangements 14a, 14b, and 14c receive a more uniform stream of light.

The length of the cylinders 20 should be sufficiently large that the incident light is totally reflected at least once at one of the walls between the end faces 19, 21. Focussing of the light leaving the light conducting rod at the same angles onto the associated end face 19 is once more preferably achieved by insertion of the lens 26 shown in broken lines. This results especially in a sharp separation between the individual angular ranges being obtained.

In the especially preferred embodiment of FIG. 7 the light leaving the light conducting rod 12 is directed by a lens system 26 and, if necessary, a light scattering device 16 onto the end faces 19 of concentrically arranged transparent truncated cones 22a, 22b, 22c of different lengths which are located one within the other. The lens system 26 ensures not only that the light is concentrated onto the end faces 19 but also that the light beams impinge at a relatively small angle onto the surfaces of the truncated cones 22.

An optical deflection of this kind by the lens system 26 is also advantageous in the embodiment of FIGS. 5 and 6.

The individual truncated cones 22a, b, c, guide the incident light by total reflection at their opposing walls to the opposite end faces 21 which, because of the various lengths of the truncated cones, are located at the same radial distance from the axis 11. The length of the truncated cones is such that only a few individual convertors 18, need to be arranged within the inner borders of the end faces of the truncated cones 22a, 22b to receive the entire light leaving the next inwardly disposed truncated cone. An interior mirror surface 24 between each end face 21 and the end face 21 of the next inwardly disposed truncated cone guarantees that light leaving the end faces 21 reaches the associated photoelectric convertor 18 in its entirety by reflection at this interior mirror surface 24. The convertors can however also be arranged directly at the inner borders of the truncated cones similarly to FIG. 5.

The exterior surface of the outermost truncated cone 22a is extended by a wall 25 which is sufficiently long that its inner end border is of the same dimensions as the inner end borders of the customary truncated cones 22. The interior of the wall 25 is also provided with an interior mirror surface. A further individual convertor is located at the end of the wall 25.

The six individual convertors 18 which can be seen in FIG. 7 are thus arranged one behind the other on the axis 11 and receive respectively the light from one of the three cones which are located one within the other. Thus it is only necessary to interconnect fewer individual convertors 18 to a photoelectric convertor arrangement that in the previous embodiment of FIGS. 3 to 6. By this construction, in accordance with the invention, a very compact arrangement is achieved which is spatially of little trouble.

The cone angle of the truncated cone is chosen such that, on taking into account the light entry angle, onward transmission of the incident light is achieved by total reflection without problems.

The interior passage of the inner truncated cone 22c can be closed by a non transmitting wall 23 in order to keep light leaving the light conducting rod at less than the specified angle away from the inner photoelectric convertor arrangement 14c.

A really especially preferred embodiment is shown in FIGS. 9 to 12. The apparatus which focusses the light from the aperture 13a, 13b or respectively 13c is comprised here of individual light guides which are constructed and united in the manner especially illustrated in FIGS. 10 and 11. Each light guide has an end face 19 which is constructed in the form of a sector of an annulus and which takes in light from a corresponding portion of the surface of the aperture 13a, 13b or respectively 13c. The individual light guides are united into annular arrangements 48a, 48b, or 14c respectively and there are six light guides for each respective periphery.

In accordance with the invention each light guide reduces from the entry end face 19 to a relatively small face 51 to which as per FIG. 9 two individual convertors 18 are respectively connected.

Gores (Vee shaped slots) 50 are found between neighbouring entry end faces 19 and in the present embodiment each have an included angle of around 15°.

All the individual convertors 18 associated with each annular arrangement, 48a, 48b or 48c are connected together to photoelectric detector arrangements 14a, 14b or 14c respectively similarly to the previous embodiments so that once more outputs 42, 43 and 44 are present which deliver three respective electrical output signals.

As can be seen especially from FIGS. 10 and 11 the inner faces of the light guides 49a, 49b, 49c form sections of a right cylinder. The exterior sides taper conically by a small amount from the entry end face 19 to the exit end face 51.

In section, along one peripheral face, the reduction is however considerably more pronounced. In this way it is taken into account that the light in the peripheral surface is relatively parallel at incidence so that, despite the relatively more pronounced degree of taper the light entering at 19 will leave in its entirety at 51.

In the radial planes the light is incident at relatively diverse angles because of the presence of the lens or respectively the lens system 26 so that guiding of the light to the exit end face 51 is only ensured by a relatively smaller degree of taper. The various angles under which the light enters the end faces 19 in radial planes can be clearly seen in FIG. 9.

The crown like arrangement of the light guides of FIGS. 9 to 12 thus optimally takes into account the conditions at the light entry to the arrangement of the invention. Altogether the angles of taper are to be chosen so that the light entering the end face 19 emerges in its entirety at 51 and is not finally reflected back on itself by too sharp a degree of taper. At 51 an optical contact with the respective convertor is necessary.

An especially advantage of the crown like construction of the light concentrating device of FIGS. 9 to 12 resides in that normal fibre light guides can be attached to the relatively small end faces 51 by means of which the light can be further transmitted to desired positions, and can especially be concentrated at the desired position, for example onto a single photodiode. The normal, attached, individual fibre light guides can be lead outwardly without furtherado through the spaces provided between the individual light guides. This applies also to the inner ring arrangements 48b and 48c.

In FIG. 12 for example it is illustrated how the fibre light guides 74 can be led to respective individual convertors 18 from the exit end faces 51 of the outer light conductors 49a. All the fibre light guides from one ring arrangement 48 can basically be led to a single small multiplier. It is however preferred that a plurality of parallel connected individual convertors (diodes) are provided with each of which a fibre light guide 74 is associated.

In the arrangement of FIGS. 9 to 12 three times six fibre light guides are thus necessary in total. The advantage of such an arrangement would reside in the considerable improvement of the homegenising effect on the output light. This is especially important with the use of inhomogenous cells or cells of various sensitivities, or also of a single small multiplier It is further necessary that an optical contact is present between the end faces 51 and the three directly connected photoelectric convertors 18 or the light guides 14. By the arrangement of FIGS. 9 to 12 a true light transformation succeeds. For choosing the angle of taper the known relationship $$F \cdot \operatorname{Sin}^2 u = F^1 \cdot \operatorname{Sin}^2 u^1 = \text{constant}$$

is to be taken into account in which F is the entry surface of the light guide u is the entry angle, $F^1$ the exit surface and $u^1$ the exit angle of the light.

The outputs 42, 43, 44 of the photoelectric convertor arrangements 14a, 14b or 14c respectively are connected as in FIG. 13 to an amplifier 29 whose amplification can be adjustable or automatically controlled.

The amplifiers 29 of the two outer convertor arrangements 14a, 14c are connected to a difference forming stage 28 whose output is passed to a video subtraction filter 30. An analog digital convertor 31 is connected to this filter.

The amplified signals of the convertor arrangements 14a, 14c are also applied to a summing stage 33 which, if necessary is connected via a damping member 45 to a further difference forming stage 32 to whose other input the amplified output signal of the inner photoelectric convertor arrangement 14b is passed.

The output signal of the difference forming stage 32 is again passed via a video subtraction filter 34 to a further analog digital convertor 35.

The difference forming in the stages 28, 32 serves to eliminate the influence of stray or background light. In the video subtraction filters 30, 34 the mean value of the input signal over a predetermined tune is subtracted from the instantaneous value so that the uniform part of the signal is removed. In the analog-digital convertors 31 or 35 respectively a 1 bit quantification can, for example, take place in order to create an alarm signal in the case of a specified deviation of the light.

The outputs of the two analog-digital convertors are applied to both inputs of an OR-gate 36 at whose output an error signal appears on the occurrence of any fault on the reflecting surface which can be further processed in a desired manner.

If for example the laser beam 38 meets a non-reflecting fleck on the reflecting surface of the web 38 then the stream of light at the middle convertor arrangement 14b disappears and an error signal appears at the output of the convertor 35 which can be extracted via the OR gate 36. If on account of a depression or bump in the surface of the web a temporal variation in the reflection occurs then either the convertor arrangement 14a or the convertor arrangement 14c receives light which results in an error signal at the output of the convertor 31 which can likewise be extracted via the OR gate 36. If desired, signals corresponding to the dark field arrangement or the bright field arrangement can be taken from 46, 47.

FIG. 14 shows a further possible interconnection of the output signals of the photoelectric convertor arrangement. The outputs 42', 43', 44' are applied via resistances to a mixing stage 52 at which a desired mixing of the signals, preferably however their addition, can take place. The error signal is then formed via a trap or buffer amplifier.

FIG. 15 shows a preferred signal processing circuit which processes the output signals of the convertor arrangements 14a, b or respectively c, in suitable manner before they are passed to the inputs 42', 43', 44' of the circuit of FIG. 14.

In FIG. 15 the output of the convertor arrangement 14a, b or c is applied to the input of an amplifier 54, whose output is connected with the one input of a difference forming stage 55. The other input of the stage 55 is connected to an earthed storage condensor 75, which via a switch 69 and a change over switch 73 can be charged with the output of the amplifier 54 or from a mean value signal M whose formation will be described in the following.

A buffer amplifier 56 and a low pass filter 57 with a switch selectable constant are connected to the difference forming stage. The output of this low pass filter is connected with the one input of a further difference forming stage 58 whose other input lies at the input of the low pass filter 57 via a potentiometer 59. The circuit members 57, 58 together form a video subtraction filter whose base frequency is smaller or the same as the frequency mix contained in the video signal. In this stage the uniform part of the video signal is eliminated so that at the output only the relevant variation in the signal is present.

The output of the difference forming stage 58 is connected via a buffer amplifier 60 to a first video output terminal 61 which gives the subtracted video signal and in particular contains information on the polarity.

The first video output terminal is further applied to a second video output terminal 65 via a balancing network 62, a rectifier 63 and also a further buffer amplifier 64 which forms the main output of the circuit and delivers a rectified video signal which is applied to the inputs 42', 43' or respectively 44' of the circuit of FIG. 14.

A further branch line leads from the output of the difference forming stage 55 to a third video output terminal 67 via a buffer amplifier 66 and onto which a control stage 68 is connected. The control stage 68 delivers the control signal TP for the low pass filter and also the signal S for the switch 69.

The output of the buffer amplifier 66 is, apart from this, connected to a fourth video output terminal 71 via a switch 72 and an integrator 70 which delivers the long time mean value signal M for the difference forming step 55.

In FIG. 16 at the beginning of a scanning period there next arises a dark impulse 76 which is succeeded by a light impulse 77 at the retro-reflecting material at the border of the material to be scanned. Subsequently there follows the material scanning stretch 78 in which two faults 79, 80 may be indicated. At the end of the web there follows a bright impulse 81 and a dark impulse 82 brought about a retro reflecting material.

The control stage 68 shuts the switch 69 during the time 83 for forming the reference potential for the difference forming stage 55. The charging of the capacitor 75 can take place either via the amplifier 54 or the output terminal 71 which is determined by a corresponding position of the change over switch 73, because of the circuit of FIG. 15.

The bright signal 77, 81 at the beginning and end of the scanning periods result in the appearance of only the actual measured signal at the output 65 which is free from the influences of changing light and also constant light.

With a diameter of the light conducting rod of from 30 to 70 millimeters and especially 50 m.m. the mean diameter of the concentric apertures 13a, 13b, 13c with imaging by way of a lens system 26 is 30 to 55, 55 to 80 and 80 to 105 millimeters respectively. The widths of the apertures should preferably be between 10 and 20 and particularly 12.5 millimeters. In this case the lengths of the cylinders 20a, 20b, 20c or of the truncated cones 22a, 22b, 22c are usefully from 100 to 200 millimeters.

If the main reflection beam or lobe of the material has an included angle normally greater than 2° and on average 5° then the angular range associated with the middle ring 13b should amount to 2° to 10° the upper limit being preferred. With such a construction the sensitivity of the apparatus is still sufficient without it being too sensitive to normal permitted tolerances of the upper surface of the web or against certain inaccuracies in the adjustment.

The apparatus of the invention can be used to especial advantage in combination with an apparatus according to the copending application having the title "Apparatus for Detecting Faults in the Reflecting Surface of a Web" (Ser. No. 913,625, filed June 8, 1978) because in this way various angular ranges in planes at right angles to each other can be taken into account, the capability of the combined apparatus is thus considerably improved.

We claim:

1. Apparatus suitable for distinuishing between predetermined ranges of angles at which light rays leave a point on a surface, the apparatus comprising a light conducting rod of substantially circular section said light conducting rod being disposed parallel to the surface for receiving light rays reflected from the point onto its surface and having means capable of transmitting said light rays to an end face of the light conducting rod and producing at the end face of the rod an angular separation of the emergent light rays, said angular separation being related to the angle of incidence of said light ray along the rod relative to the optical axis thereof, there being further provided several photoelectric detector arrangements spaced apart from the end face of said light conductng rod and each disposed to receive the light from at least a major portion of a respective one of a series of annular apertures through which said angularly separated light leaving said light conducting rod passes, each said aperture and its associated detector being associated with a particular range of angles.

2. Apparatus according to claim 1 and in which the number of said photoelectric detector arrangements lies in the range 2 to 4.

3. Apparatus according to claim 1 and in which there is provided three photoelectric detector arrangements.

4. Apparatus according to claim 3 and in which the curvature of said light conducting rod lies in the range 30 to 70 mm and the mean diameters of the concentric apertures associated with each said photoelectric detector arrangement lies in a range between 20 and 55, 55 and 80 and 80 to 105 mm.

5. Apparatus according to claim 4 and in which the width of each aperture lies in the range from 10 to 20 mm.

6. Apparatus according to claim 5 and in which the width of each said aperture equals 12.5 mm.

7. Apparatus according to claim 3 adapted for recognizing faults in said surface, said surface having an indicatrix with a pronounced main reflection beam there being further provided means for linewise scanning said surface with a sharply defined light ray, said light conducting rod being arranged parallel to the direction of scanning and in which the output signal from each of the said three photoelectric detector arrangements are passed a mixing stage, there being means for taking an output signal from a buffer amplifier connected to said mixing stage.

8. Apparatus according to claim 7 and in which said mixing stage sums the three output signals.

9. Apparatus according to claim 8 and in which the output signal of each photoelectric detector arrangement is applied to said mixing stage via an active low pass filter, said active low pass filter having an adjustable time constant, and via an amplifier and a difference forming stage and a buffer amplifier, the output from said low pass filter being supplied to a further difference forming stage to the other input of which is passed the input potential of the low pass filter via a potentiometer 59 and whose output is further applied to the first video output terminal via a further amplifier.

10. Apparatus according to claim 9 and in which, in the first said difference forming stage, there is formed the difference between an instantaneous value of the video signal and a mean value of the video signal formed over one or move scanning periods thereof.

11. Apparatus according to claim 10 and in which the output of said first video output terminal is applied to a balancing stage and the output of said balancing stage is led to a second video output terminal via a rectifier and a further amplifier.

12. Apparatus according to claim 11 and in which the output of the first difference forming step leads to a third video output terminal via a further buffer amplifier.

13. Apparatus according to claim 12 and in which a control stage is connected to said third video output terminal, said control stage delivering output signals for controlling said mean value switch and said active low pass filter.

14. Apparatus according to claim 13 and in which said further buffer amplifier is connected to a fourth video output terminal via a long time integrator.

15. Apparatus according to claim 14 and in which a change over switch is provided for connecting said fourth video output terminal to said mean value input of the first difference forming stage.

16. Apparatus according to claim 1 and further comprising light scattering means disposed downstream of the end face of said light conducting rod for producing a fanning out of the individual light rays associated with each said aperture.

17. Apparatus according to claim 1 and in which each said photoelectric detector arrangement comprises a series of individual photoelectric convertors collectively arranged to sense the said respective aperture as fully as possible and means interconnecting said individual photoelectric convertors to produce a single electrical output signal.

18. Apparatus according to claim 1 including a plurality of respective transparent light conducting means disposed one in front of each said photoelectric convertor arrangement for guiding light received from a respective said aperture onto the respective photoelectric detector arrangement.

19. Apparatus according to claim 18 and in which said plurality of transparent light conducting means comprises a series of concentric transparent cylinders.

20. Apparatus according to claim 18 and in which each said photoelectric detector arrangement comprises a series of interconnected individual converters contacting one end face of the said respective transparent light conductor.

21. Apparatus according to claim 18 and in which said plurality of transparent light conducting means comprises a series of concentric transparent truncated cones.

22. Apparatus according to claim 21 and in which the length of said truncated cones reduce in stepwise fashion from outer to inner and wherein said photoelectric detector arrangements associated with the individual truncated cones are arranged axially one behind the other.

23. Apparatus according to claim 22 and in which each photoelectric detector arrangement is arranged axially spaced apart from the associated end face of the respective truncated cone.

24. Apparatus in accordance with claim 23 and in which each respective photoelectric detector arrangement associated with one of said truncated cones is arranged at the inside end border of the next outer truncated cone.

25. Apparatus according to claim 24 and in which the exterior surface of the outermost truncated cone is extended by a wall which continues its truncated cone shape to an associated photoelectric detector arrangement and that the inner end borders of each of said truncated cones are of the same size.

26. Apparatus according to claim 22 and in which each said photoelectric detector arrangement comprises a single individual photoelectric converter.

27. Apparatus according to claim 22 and in which each said photoelectric detector arrangement comprises two individual photoelectric convertors.

28. Apparatus according to claim 22 and in which the inner wall of each said truncated cone extending beyond the end face of the next inner truncated cone is provided with a mirror surface on said inner wall extending from the end face of the next inner truncated cone to its own end face.

29. Apparatus according to claim 28 and in which the exterior surface of the outer-most truncated cone is extended by a wall said wall continuing the truncated cone shape and being provided with an internal mirror surface extending from the end face of said outer-most truncated cone to the respective said associated photoelectric detector arrangement.

30. Apparatus according to claim 18 and in which each of said transparent conducting means comprises a series of tapering transparent light guides.

31. Apparatus according to claim 30 and in which the end faces of said tapering transparent guides are sectors of annuli.

32. Apparatus according to claim 31 and in which respective radially inner edges of adjacent transparent light guides of each of said series of light guides lay adjacent each other at the ends of the light guides remote from the respective photoelectric detector arrangements.

33. Apparatus according to claim 32 in which there is provided a space between the radially outer edges of adjacent transparent light guides of each of said series of light guides at their ends remote from the respective photoelectric detector arrangements.

34. Apparatus according to claim 33 and in which a gore shaped space of substantially 15° C. is present between adjacent radially inner and outer adjacent transparent light guide of each of said series of transparent light guides.

35. Apparatus according to claim 34 and in which the width of each said tapering transparent light guide along its peripheral surface reduces to a value less than its original width said value lying in the range ½ to 1/7.

36. Apparatus according to claim 35 and in which said value comprises 1/5.

37. Apparatus according to claim 30 and in which the number of said tapering transparent light guides associated with each aperture lies in the range from four to eight, said light guides being regularly distributed to receive light from the respective aperture.

38. Apparatus according to claim 37 and in which six said tapering light guides are associated with each said aperture.

39. Apparatus according to claim 30 in which each of said tapering transparent light guides tapers less in a radial section than across its width.

40. Apparatus according to claim 39 and in which the radially inner surfaces of each of said series of tapering transparent light guides follow the surface of a right cylinder.

41. Apparatus according to claim 40 and in which the radially outer surfaces of said light guides converge slightly conically whereby the radial depth of each of said tapering transparent light guides reduces over its length to one half of its original radial depth.

42. Apparatus according to claim 30 and in which the exit end faces of the light guides are sectors of annuli.

43. Apparatus according to claim 30 in which the taper of said light guide is chosen so that light rays entering at the light entry side of the said transparent light guides emerge completely at the other end face of the respective said transparent tapering light guide.

44. Apparatus according to claim 30 and in which one end of each of a series of fibre optic light guides is connected to a respective exit end face of each of said tapering transparent light guides and said photoelectric detector arrangements being connected to the other ends of the fibre optic light guides.

45. Apparatus according to claim 18 and in which the length of said light conducting means lies in the range from 100 to 200 mm.

46. Apparatus according to claim 18 and in which the length of said photoelectric detector arrangement detects light normally reflected from said surface.

47. Apparatus according to claim 1 and in which each of said photoelectric detector arrangements is of the same size and construction.

48. Apparatus according to claim 1 and in which a lens system is disposed downstream of the end face of the light conducting rod and upstream of each of said photoelectric detector arrangements.

49. Apparatus according to claim 48 and in which the said lens system concentrates the light leaving the light conducting rod onto the said respective associated apertures.

50. Apparatus according to claim 48 and in which the lens system deflects the light passing through each said aperture whereby to subtend the smallest possible angle to the longitudinal surfaces of any respective light guide disposed in front of the respective photoelectric detector arrangement.

51. Apparatus according to claim 1 and in which said means capable of transmitting said incident light to an end face of the light conducting rod for producing at the end face thereof an angular separation of the emergent light rays comprises a series of convexly curved individual mirrors disposed in a line each individual lens being obliquely aligned to the rod axis.

52. Apparatus according to claim 51 and in which the degree of said convex curvature is such that a parallel light beam incident on the individual mirror after reflection in the plane of curvature is fanned out through an angle lying in the range from 10° to 90°.

53. Apparatus according to claim 52 and in which said angle comprises 50°.

54. Apparatus according to claim 1 and adapted for the recognition of faults in said surface, said surface comprising a reflective material having an indicatrix with pronounced main reflection beam said apparatus further comprising means for directing a sharply defined laser light beam continually onto said surface for linewise scanning thereof said light conducting rod being arranged parallel to the scanning direction and in which the photoelectric detector arrangements associated a pair of said apertures are connected to a difference forming stage, each of said pair of apertures receiving light reflected from said surface to either side of the normal reflected beam from said surface.

55. Apparatus according to claim 54 and in which the output of said difference forming stage is connected to a video subtraction filter.

56. Apparatus according to claim 55 and in which an analog digital convertor follows the video subtraction filter.

57. Apparatus according to claim 54 and in which a further photoelectric detector arrangement disposed to receive light from an aperture associated with the normally reflected beam from said surface, is connected to a further difference forming stage to the second input of which is passed a summed signal formed from the sums of the signals of the other said pair of photoelectric convertor arrangements.

58. Apparatus according to claim 57 and in which the output of said further difference forming stage is connected to a further video subtraction filter.

59. Apparatus according to claim 58 and in which said further video subtraction filter is followed by a further analog-digital convertor.

60. Apparatus according to claim 59 and in which the outputs of both said analog-digital convertors are connected to the two inputs of an OR gate.

* * * * *